US00PP11278P

United States Patent [19]

Pouw

[11] Patent Number: Plant 11,278

[45] Date of Patent: Mar. 7, 2000

[54] HYBRID TEA ROSE PLANT NAMED 'RUIPINVI'

[75] Inventor: A. A. Pouw, Pl De Kwakel, Netherlands

[73] Assignee: De Ruiter's Nieuwe Rozen B.V., Pl De Kwakel, Netherlands

[21] Appl. No.: 09/028,615

[22] Filed: Feb. 24, 1998

[51] Int. Cl.[7] ..... A01H 5/00

[52] U.S. Cl. ..... Plt./137

[58] Field of Search ..... Plt./137, 138, 130, Plt./132

*Primary Examiner*—Howard J. Locker
*Attorney, Agent, or Firm*—Christie, Parker & Hale, LLP

[57] ABSTRACT

A new variety of hybrid tea rose plant producing pink flowers of good form.

2 Drawing Sheets

BACKGROUND OF THE INVENTION

The present invention relates to a new and distinct variety of rose plant of the hybrid tea rose class which was created by crossing undistributed, unnamed and unpatented seedlings as seed and pollen parents in The Netherlands. The varietal denomination of the new variety is 'Ruipinvi'.

SUMMARY OF THE INVENTION

Among the novel characteristics possessed by this new variety which distinguish it from its parents and all other varieties of which I am aware are its attractive pink flowers with long stems borne on a floriferous plant.

Asexual reproduction by budding of the new variety as performed in The Netherlands, shows that the foregoing and other distinguishing characteristics come true to form and are established and transmitted through succeeding propagations. The new variety has been reproduced through propagation by cuttings, grafting, budding and micropropagation.

BRIEF DESCRIPTION OF ILLUSTRATIONS

The accompanying two photographic illustrations show the new variety of hybrid tea rose plant in color as true as it is reasonably possible to attain in color illustrations of this character.

The first illustration is a close up view of the bloom, peduncle, and foliage.

The second illustration shows a new shoot, 1; compound 3-leaflet leaf, 2; compound 5-leaflet leaf (partially cut-off), 3; compound 7-leaflet leaf, 4; a stem, 5; buds, 6 and 7; a flower about ⅓ to ½ open, 8; a flower fully open, 9; and flower stems 10, 11, and 12, with reproductive organs displayed.

DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart. Phenotypic expression may vary depending upon growing conditions under different climate, soil, and cultivation conditions.

Parentage: Seed and pollen parents are unnamed seedlings. Class: Hybrid Tea.

The following further horticultural description is based on observations made of specimens grown under glass in Quito, Ecuador.

FLOWER

Blooming habit: Nearly continuous.

A. Bud:

(1) *Size.*—Medium, about 5 cm long by about 3 to 4 cm wide, before sepals fall. About 5 cm long by about 3 to 5 cm wide, after sepals separate further.

(2) *Form.*—Ovate (shape of longitudinal section just before separation of sepals); urn-shaped after sepals part and petals begin to separate.

(3) *Color.*—Before sepals separate, near 62A through 62D, deeper tones washing toward petal edges becoming lighter toward point of petal attachment.

(4) *Sepals.*—Some longer than bud, some foliaceous; green, near 178A purple at edge and tips.

(5) *Peduncle.*—Long; srength-erect, strong. Color green, near 138BC.

B. Flower: Medium; viewed from side -(a) upper part of fully opened flower, flattened convex; (b) lower part of fully opened flower, concave.

(1) *Size.*—Average size when fully expanded - about 10 to 12 cm.

(2) *Borne.*—Singly, one to a stem.

(3) *Form.*—Pointed, high center, exhibition form, spiral imbricated, outer petals reflex to points, some inner petals reflex to points and some roll under.

(4) *Petalage.*—Fully double, about 30.

(5) *Color.*—After sepals part and petals unfurl color of petal top surface is near 62A to 62B to 62C to 62D, with deeper tones at outer petals and lighter tones at flower center, deep tones also at petal edge washing in lighter tones in petals toward point of petal attachment; veining also seen with deeper tones at veins; petal under surface, near 54B to 54C display deeper tones at petal edges washing into lighter tones to lower portions of petals. Color at point of petal attachment is near 4C. Overall tonality from a distance is attractive pink flowers.

(6) *Peduncle.*—Generally smooth.

(7) *Fragrance.*—Weak.

(8) *Length of Stems.*—About 60 cm to 100 cm.

Petals:

(1) *Texture.*—Crisp.

(2) *Appearance.*—Inside velvety and outside satiny.

(3) *Form and Size.*—Broad, undulated margin.

(4) *Arrangement.*—Regularly arranged, imbricated.

(5) *Petaloids.*—About 15.

(6) *Lasting quality.*—Long-lasting quality on plant (about 18 days) and after cutting (about 12 days).

REPRODUCTIVE ORGANS

A. Stamens, filaments and anthers:

*Arrangement and color.*—Regularly arranged around styles; color of filaments — orange red.

B. Pollen: Color — yellow.

C. Styles: Long, stigma above mouth of receptacle, white.

D. Stigmas: Yellow.

E. Hip: Pitcher-shaped; medium seed vessel at petal fall.

PLANT

A. Form: Narrow, bushy, average disease resistance; height about 1.6 m, spread about 0.5 m.

B. Growth: Vigorous.

C. Foliage: Compound 3, 5 and 7 leaflets.

(1) *Size.*—3-leaflet leaf, terminal leaflet about 8 cm long; 5-leaflet leaf, terminal leaflet about 8 to 9 cm long; 7-leaflet leaf, terminal leaflet about 8 to 9 cm long.

(2) *Quantity.*—Abundant.

(3) *Color.*—Juvenile foliage — near 187A and near 181A to 181B underside; medium anthocyanin coloration, (shoot about 20 cm long); mature leaf color — top near 186A, underside near 136C to 187A.

(4) *Shape.*—Broad oval.

(5) *Texture.*—Upper side is medium glossy; underside is matte.

(6) *Edge.*—Serrate.

(7) *Serration.*—Ordinary, acuminate apices.

(8) *Leaf stem.*—Color — dark green with brown cast.

(9) *Stipules.*—About 1 cm, green color same as leaves and light green control mid-line.

(10) *Leaflets.*—Cross section — slight concave; weak to medium undulation of margin; terminal leaflet — medium length and medium width; rounded base.

D. Wood:

(1) *New wood.*—Color — young shoots have weak anthocyanin; coloration — reddish brown to purple.

(2) *Old wood.*—Color — near 136A.

E. Prickles (thorns):

(1) *Prickles.*—Present; shape of lower side — concave; Short prickles absent or very few; prickles on juvenile shoots near 178A, prickles on adult shoots near 178B. Position — irregular.

What is claimed is:

1. A new and distinct hybrid tea rose plant of the variety substantially as shown and described.

* * * * *

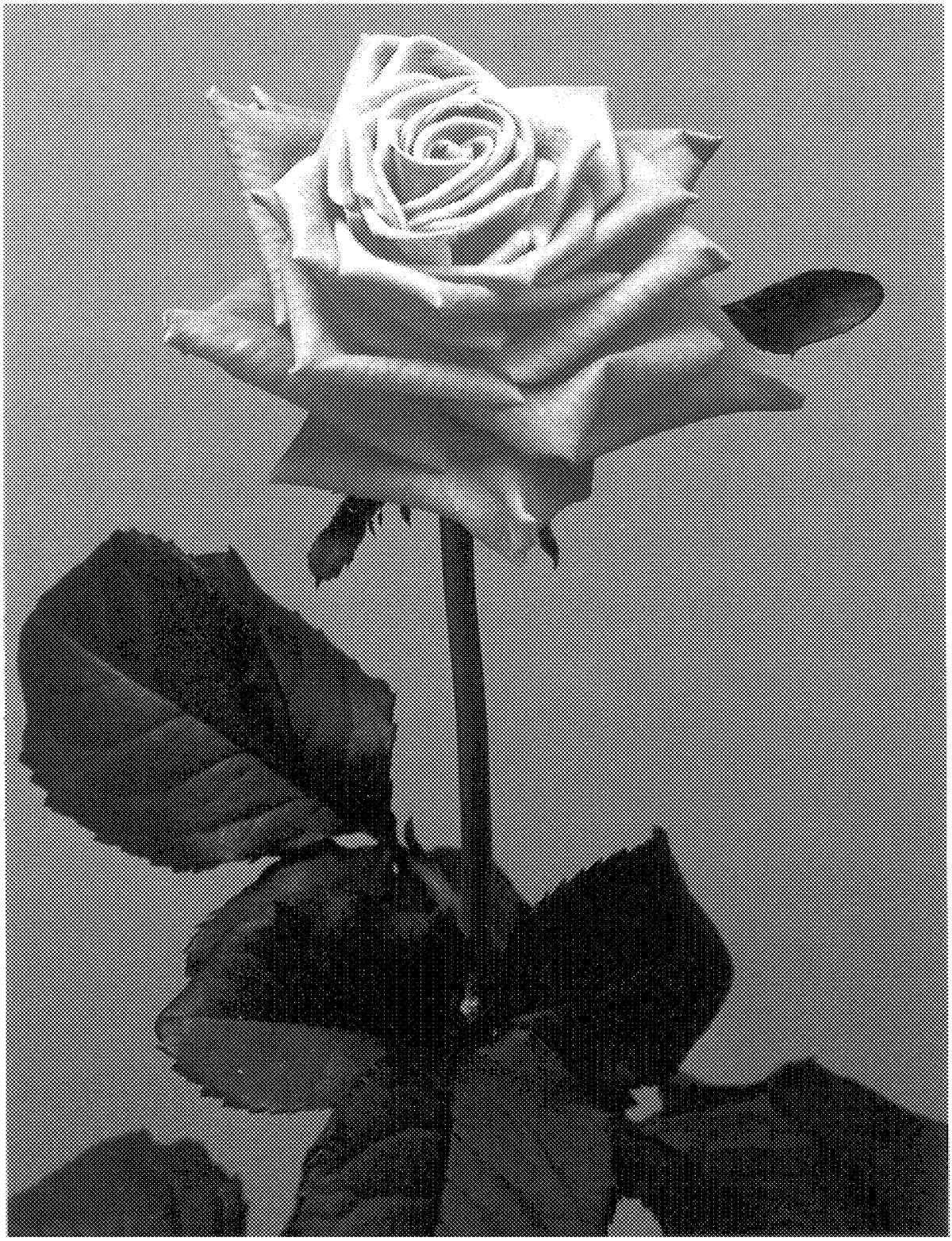

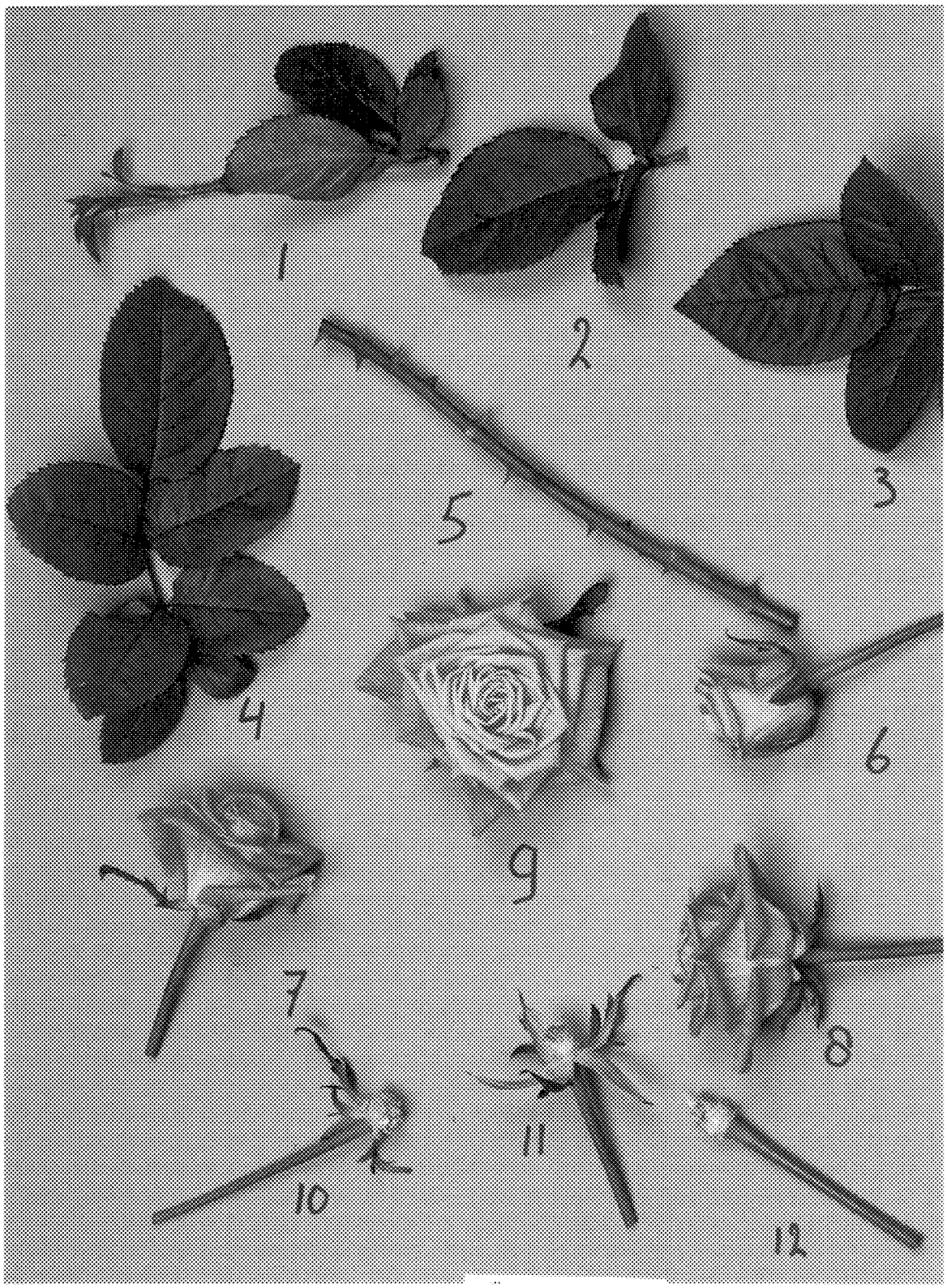
1
2
3
4
5
6
7
8
9
10
11
12